United States Patent
Lai et al.

(10) Patent No.: US 10,772,502 B2
(45) Date of Patent: Sep. 15, 2020

(54) NON-INVASIVE INTRAOCULAR PRESSURE MONITOR

(71) Applicants: Queen's University at Kingston, Kingston (CA); Kingston Health Sciences Centre, Kingston (CA)

(72) Inventors: Yong Jun Lai, Kingston (CA); Kong Ying Xie, Kingston (CA); Robert James Campbell, Kingston (CA)

(73) Assignees: Queen's University at Kingston, Kingston, ON (CA); Kingston Health Sciences Centre, Kingston, ON (CA)

( * ) Notice: Subject to any disclaimer, the term of this patent is extended or adjusted under 35 U.S.C. 154(b) by 666 days.

(21) Appl. No.: 15/461,881

(22) Filed: Mar. 17, 2017

(65) Prior Publication Data
US 2017/0280997 A1 Oct. 5, 2017

Related U.S. Application Data
(60) Provisional application No. 62/310,432, filed on Mar. 18, 2016.

(51) Int. Cl.
*A61B 3/16* (2006.01)
*A61B 3/14* (2006.01)
(Continued)

(52) U.S. Cl.
CPC .................. *A61B 3/16* (2013.01); *A61B 3/14* (2013.01); *A61B 5/0077* (2013.01);
(Continued)

(58) Field of Classification Search
CPC ........... A61B 3/14; A61B 3/16; A61B 5/0077; A61B 5/6821; A61B 2562/028
See application file for complete search history.

(56) References Cited

U.S. PATENT DOCUMENTS

| 9,247,877 B2 | 2/2016 | Elsheikh et al. |
| 2011/0288395 A1 | 11/2011 | Elsheikh et al. |

(Continued)

FOREIGN PATENT DOCUMENTS

CN 105919551 B 7/2017

OTHER PUBLICATIONS

Dimitrov, P.N. et al., "Five-year incidence of bilateral cause-specific visual impairment in the Melbourne visual impairment project", Invest. Ophthalmol. Vis Sci. 44, pp. 5075-5081, (2003).
(Continued)

*Primary Examiner* — Devin B Henson
(74) *Attorney, Agent, or Firm* — Stephen J. Scribner (57) ABSTRACT

The invention provides devices and methods for non-invasive monitoring and measuring of intraocular pressure (IOP) of a subject. Embodiments include a lens that is adapted to fit on the subject's eye, a microstructure disposed in or on the lens, the microstructure having at least one feature that exhibits a change in shape and/or geometry and/or position on the lens in response to a change in curvature of the lens. When the curvature of the lens changes in response to a change in IOP, a corresponding change in shape and/or geometry and/or position of the feature may be used to determine the change in IOP. The change in the feature is detectable in digital images of the lens taken with a mobile electronic device such as a smartphone.

8 Claims, 12 Drawing Sheets

(51) Int. Cl.
A61B 5/00 (2006.01)
A61B 90/00 (2016.01)
(52) U.S. Cl.
CPC .......... *A61B 5/6821* (2013.01); *A61B 5/6898* (2013.01); *A61B 2090/3937* (2016.02); *A61B 2562/028* (2013.01)

(56) References Cited

U.S. PATENT DOCUMENTS

| | | | |
|---|---|---|---|
| 2015/0087953 A1* | 3/2015 | Chiou | A61B 3/16 600/398 |
| 2016/0015265 A1 | 1/2016 | Mandel et al. | |

OTHER PUBLICATIONS

VanNewkirk, M.R. et al., "Cause-specific prevalence of bilateral visual impairment in Victoria, Australia: The visual impairment project", Ophthalmology, 108, pp. 960-967, (2001).
Liu, J.H.K. et al., "Monitoring intraocular pressure for 24", Br J Ophthalmol 95: pp. 599-600, (2011).
Weinreb, R.N. et al., "Nocturnal rhythms of intraocular pressure", Arch Ophthalmol. pp. 124:pp. 269-270, (2006).
Bagga, H. et al., "Intraocular pressure measurements throughout the 24 h", Curr. Opin. Opthalmol. vol. 20, Issue 2, pp. 79-83, (2009).
Weinreb, R.N. et al., "Intraocular Pressure" Reports and Consensus Statements of the 4th Global Aigs Consensus Meeting on Intraocular Pressure. The Hague, The Netherlands: Kugler, 2007,WGA Consensus Series 4 pp. 1-148.
Shiose Y. "The aging effect on intraocular pressure in an apparently normal population", Arch Ophthalmol. Jun.;102(6):883-7, (1984).
Chen, P. et al., "Unpowered spiral-tube parylene pressure sensor for intraocular pressure sensing", Sensors and Actuators A 127 pp. 276-282, (2006).
Clark, R. A., et al., "Deformations and stresses in Bourdon tubes", J. Appl. Phys. 21(12) pp. 1340-1341,(1950).
Lin. J. C-H. et al., "High Quality Factor Parylene-Based Intraocular Pressure Sensor", NEMS 2012, Kyoto, Japan, Mar. 5-8, 2012.
Mansouri K. et al., "Continuous intraocular pressure monitoring with a wireless ocular telemetry sensor: initial clinical experience in patients with open angle glaucoma", Br. J. Ophthalmology 95, pp. 627-629, (2011).
Leonardi, M., et al., "First Steps toward Noninvasive Intraocular Pressure Monitoring with a Sensing Contact Lens", Investigative Ophthalmology & Visual Science, 45(9) 3113-3117, (2004).
Sanchez, I., et al, "Prototype of a Nanostructured Sensing Contact Lens for Noninvasive Intraocular Pressure Monitoring", Investigative Ophthalmology & Visual Science, vol. 52, No. 11, pp. 8310-8315, (2011).
Lam, A K.C. et al., "The effect of an artificially elevated intraocular pressure on the central corneal curvature", Ophthal. Physiol. Opt. vol. 17, pp. 18-24, (1997).
Leonardi, M., et al., "Wireless contact lens sensor for intraocular pressure monitoring: assessment on enucleated pig eyes", Acta Ophthalmol. vol. 87, pp. 433-437, (2009).
Shin, I.H., et al., "Comparison of OCT and HRT findings among normal, normal tension glaucoma, and high tension glaucoma", Korean J Ophthalmol. vol. 22, pp. 236-241, (2008).
Bruinsma, G.M., et al., "Bacterial adhesion to surface hydrophilic and hydrophobic contact lenses", Biomaterials, vol. 22, pp. 3217-3224, (2001).
Araci, I.E., et al., "An Implantable Microfluidic Device for Self Monitoring of Intraocular Pressure", Nature Medicine, vol. 20, No. 9, pp. 1074-1078, (2014).
Mansouri, F., et al., "Continuous 24-hour monitoring of intraocular pressure patterns with a contact lens sensor", Arch Ophthalmol., vol. 130, No. 12, pp. 1534-1539, (2012).
http://money.usnews.com/money/retirement/articles/2012/01/09/65-and-older-population-soars (2013). Brandon, E. U.S. News, Jan. 9, 2012.
Molaei, A., et al., "Upcoming Methods and Specifications of Continuous Intraocular Pressure Monitoring Systems for Glaucoma", Journal of Opthalmic and Vision Research, vol. 3, issue 1, pp. 66-71, (2018).
Araci, I.E., et al., "An implantable microfluidic device for self-monitoring of intraocular pressure", Nature Medicine, vol. 20, No. 9, pp. 1074-1079, (2014).

* cited by examiner

NON-INVASIVE INTRAOCULAR PRESSURE MONITOR

RELATED APPLICATION

This application claims the benefit of the filing date of application Ser. No. 62/310,432, filed Mar. 18, 2016, the contents of which are incorporated herein by reference in their entirety.

FIELD

This invention relates to non-invasive wearable devices for monitoring and measuring intraocular pressure.

BACKGROUND

Intraocular pressure (IOP) is a critical factor that is used to monitor the health of the eyes. High intraocular pressure (IOP) is associated with glaucoma, a leading cause of blindness. Lowering IOP is currently the only evidence-based treatment for preventing the development of glaucoma or reducing the rate of its progression.

An individual's IOP may vary significantly throughout the day. There are considerable data showing that the IOP peaks of many glaucoma patients occur outside daytime hours when IOP is usually measured. As peak IOP is related to glaucoma progression, this suggests that IOP measurements outside office hours should be taken into account when clinicians plan and prescribe glaucoma treatment. However, IOP measurements are typically conducted by professionals during eye examinations during regular business hours and only at relatively infrequent intervals, leading to a need for more accessible IOP measurement technology that provides frequently repeated IOP measurements, The need for IOP monitoring in the population is growing rapidly as recognition of the importance of IOP control grows. Moreover, the population living with glaucoma or with raised IOP and consequently at risk of glaucoma, is growing in many countries as a result of the link between IOP and age in combination with aging populations, To address this need, implantable pressure sensors for IOP monitoring have been proposed. For example, a microelectromechanical system (MEMS)-based passive pressure sensor was designed to be implanted inside of the anterior chamber of the eye. However, deployment of such a device presents significant challenges in requiring invasive surgery, and careful selection of its location in the eye, A micromachined capacitive pressure sensor has also been proposed, which includes circuitry that produces a phase shift in a resonant frequency to detect a change in IOP. However, this device &so requires surgery to insert the device into the anterior chamber of the eye, and specialized equipment such as an inductive coil and impedance reader must be used to obtain the phase shift information to determine IOP. A microfluidic device using a micro channel filled with gas surgically implanted in the anterior chamber of the eye was also proposed, whereby a mobile device such a smartphone could be used to take images of the aqueous humor position in the channel.

As a result less invasive approaches are desirable, One approach proposed a contact lens with a micromachined strain gauge to measure IOP. However, this design required an electrical wire connection from the strain gauge to measuring equipment. Another used a wireless ocular telemetry sensor to monitor IOP fluctuation over a 24 hour period. This sensor required sophisticated reading equipment, and only provided an indication of a fluctuation in IOP, rather than an actual measurement of the pressure. A nano-structured sensor using piezoresistive film on a contact lens has been proposed, which also required an electrical wire connection from the piezoresistor to measuring equipment. Another approach using a contact lens and telemetry detects circumferential changes in the area of the corneo-scleral junction of the eye. A flexible adhesive antenna worn around the eye wirelessly receives a signal from the contact lens, which is provided to a portable recorder, such that information is continuously acquired. Consequently, users (patients) must wear the antenna and carry a specialized electronic device for data acquisition.

Overall, the prior approaches are either invasive or require specialized electronic equipment to obtain the measurement data, which reduce the patient's comfort, and increase the complexity and cost of clinical implementation.

SUMMARY

One aspect of the invention relates to a device for monitoring intraocular pressure (IOP) of a subject, comprising: a lens that is adapted to fit on the subject's eye; a microstructure disposed in or on the lens; at least one feature of the microstructure that exhibits a change in shape and/or geometry and/or position on the lens in response to a change in curvature of the lens; wherein the lens is adapted to change curvature in response to a change in IOP; wherein the change in shape and/or geometry and/or position of the feature is detectable in digital images of the lens, or of a part of the lens.

In one embodiment, the microstructure comprises: a sealed chamber; a sealed microchannel in communication with the chamber; an indicator solution disposed in the chamber; wherein the feature that is detectable is the indicator solution in the microchannel in response to a force applied to the chamber. According to this embodiment, the force applied to the chamber results from a change in curvature of the lens.

In one embodiment, the microstructure comprises: a motion amplifying mechanism including a free-moving arm; wherein a position of the arm is related to the curvature of the lens; wherein the feature that is detectable is a change in the position of a tip of the arm in response to a change in curvature of the lens.

In one embodiment, the microstructure comprises: two or more markers disposed in a spaced relationship on the lens; Wherein a distance between the two or more markers is related to curvature of the lens; wherein the feature that is detectable is a change in the distance between the two or more markers in response to a change in curvature of the lens. The markers may be holes or divots in the lens, or the markers may comprise dye or pigment disposed on the lens, or a combination of any of these.

The embodiments may further comprise a reference structure; wherein the reference structure has a selected size and/or position and/or shape that is Substantially constant irrespective of a change in curvature of the lens in response to a change in IOP.

According to the embodiments, the digital images may be captured using a digital camera of a personal or mobile electronic device, such as a smartphone.

Another aspect of the invention relates to a method for monitoring intraocular pressure (IOP) of a subject, comprising: disposing a microstructure in or on a lens that is adapted to fit on the subject's eye, the microstructure having at least one feature that exhibits a change in shape and/or geometry and/or position on the lens in response to a change in curvature of the lens, wherein the curvature of the lens changes in response to a change in IOP; obtaining two or more digital images of the lens, or a part of the lens, at two or more instants in time; detecting a change in shape and/or geometry and/or position of the at least one feature in the digital images; and correlating the change in shape and/or geometry and/or position of the at least one feature with IOP.

In various embodiments, the method comprises using a lens including any one of; or combination of, microstructures described herein, The method may further comprise quantifying a change in shape and/or geometry and/or position of the at least one feature in the digital images using a reference structure; wherein the reference structure is embedded or integrated in the lens and has a selected size and/or position and/or shape that is substantially constant irrespective of a change in curvature of the lens in response to a change in IOP.

The method may include capturing the digital images using a digital camera of a personal or mobile computing device, such as a smartphone.

Another aspect of the invention relates to a non-transitory computer-readable medium, comprising instructions stored thereon, that when executed on a processor, direct the processor to perform one or more steps of an algorithm for acquiring and analyzing images of an IOP measuring device as described herein, and providing an output comprising an indication of the subject's IOP at a given time, and/or of a change in IOP over time.

BRIEF DESCRIPTION OF THE DRAWINGS

For a greater understanding of the invention, and to show more clearly how it may be carried into effect, embodiments will be described, by way of example, with reference to the accompanying drawings, wherein:

FIGS. 1A and 1B are diagrams of an IOP measuring device according to one embodiment, wherein

FIGS. 2A-2D are diagrams showing preparation of a planar prototype of lens with a microstructure according to one embodiment, wherein

DETAILED DESCRIPTION OF EMBODIMENTS

Embodiments described herein address the drawbacks of prior IOP measuring approaches by providing non-invasive and low cost devices that are easily and conveniently interfaced with readily available equipment. Furthermore, the embodiments also address the need to obtain IOP data more frequently, and outside of regular office hours, since the embodiments allow subjects to obtain measurement data themselves using readily available equipment such as a smartphone or tablet computer.

In general, embodiments are non-invasive and are based on a contact lens or cosmetic lens, in and/or on which is disposed a microstructure. The microstructure has at least one feature that exhibits a change in shape and/or geometry and/or position on the lens in response to a change in IOP. The change in shape and/or geometry and/or position of the one or more feature may be recorded by images captured by a camera. Analysis of the images provides a correlation of the change in shape and/or geometry to a change in IOP, and/or a measurement of IOP. The images may be taken using a digital camera of a mobile device such as a smart phone, tablet, or laptop computer, etc., and therefore, the image may be easily taken by the subject without the need for specialized equipment and at any time of the day or night, without a professional's intervention. Further, an application running on the mobile device or remotely may include an algorithm that provides the image analysis, and may provide substantially instant feedback about the subject's IOP.

As used herein, the term "lens" refers to any type of lens that may be fitted to and worn on the eye, such as, for example, a contact lens or a cosmetic lens. A lens may fit substantially only on the cornea, or a lens may fit on the cornea and extend outwardly from the cornea to also fit over a portion of the conjunctiva and sclera. Embodiments may be constructed using a flexible polymer material suitable for lens applications such as silicone polydimethyl siloxane (PDMS)). Other materials such as polymethyl methacrylate (PMMA) may be used in some embodiments, although such material is less flexible. In some embodiments a readily available (i.e., off-the-shelf) lens is used, which is machined or modified to obtain the desired microstructure. Embodiments may be constructed by one or more of: molding a lens including a microstructure; machining a microstructure into a lens; and applying a microstructure to a lens. Molding may include preparing a 3D mold with the microstructure features (e.g., a microchamber, microchannel, or motion amplifier) using a highspeed micromilling machine. A microstructure that is applied to a lens may be an off-the-shelf structure, or it may be prepared with a micromachining process or with 3D printing technology using a material such as, but not limited to, Nylon™ or a thermoplastic polymer such as acrylonitrile butadiene (ABS).

One or more features of the microstructure has a dimension that is selected such that the change in shape and/or geometry and/or position of the feature, in response to a selected amount of change in IOP, is detectable in an image captured by a digital camera. That is, to detect a change in IOP of, e.g., 1 mmHg, the corresponding change in shape and/or geometry and/or position of the feature must be large enough to be detected in a digital image taken by a camera in a typical device of a subject wearing the lens. For example, the change in shape and/or geometry and/or position of the feature is detectable by the image analysis software in images taken by a camera having a resolution typical of a smartphone camera.

In some cases detection may be improved by attaching an external magnifier to the camera. (As used herein, "external magnifier" refers to a type of lens that is attached to the camera, and this term is used to avoid confusion with the term "lens", defined above, that is worn on the eye.) The external magnifier may be custom made to provide the desired resolution. Such a configuration can provide a resolution of at least 2~3 μm/pixel. An external magnifier may easily and inexpensively be prepared from a polymer such as polydimethylsiloxane (PDMS), and removably attached to a smartphone. For example, an external magnifier made from a drop of PDMS cured at 215.6° C. has a focal length of approximately 7.23 mm, a radius of 2.875 mm and maximum cone angle of 44.48° C., and a numerical aperture (NA) of 0.37, which is close to the NA (0.42) of a 20× microscope objective. In preliminary tests, a smartphone (iPhone® 6) had a resolution of 0.69 μm/pixel using such a PDMS external magnifier. Accordingly, the microstructures described herein may be used to detect subtle changes in IOP (e.g., 1 mmHg or less) by observing a change in shape and/or geometry and/or position of a feature of the microstructure in images captured by a digital camera of a smartphone or other common device.

Another aspect of the invention provides a non-transitory computer-readable medium, comprising instructions stored thereon, that when executed on a processor, direct the processor perform one or more steps of an algorithm for acquiring and analyzing images of an IOP measuring device as described herein, and providing an output comprising an indication of the subject's IOP at a given time, and/or of a change in IOP over time. In one embodiment, the software has two components: (1) an imaging processing algorithm; and (2) a data management algorithm. The data management algorithm may communicate with a remote server located in a physicians' office or a hospital, to perform functions such as uploading data to the remote server. In one embodiment the software may be implemented in Java, and Objective-C may be used to for Android® and iOS®-based mobile devices, in one embodiment C# and asp,net may be used to develop data management programs on the server, and the database may be created and maintained using MS SQL. The software may be executed on the processor of a mobile computing device such as a smartphone. Embodiments may include a user interface (e.g., a graphical user interface (GUI)), and may include functions associated with setup, communications, acquiring images, calibration, measurement, and review, including outputting/displaying results/images on a display screen of the device, such as, for example, those shown FIG. 7.

Figure 7:
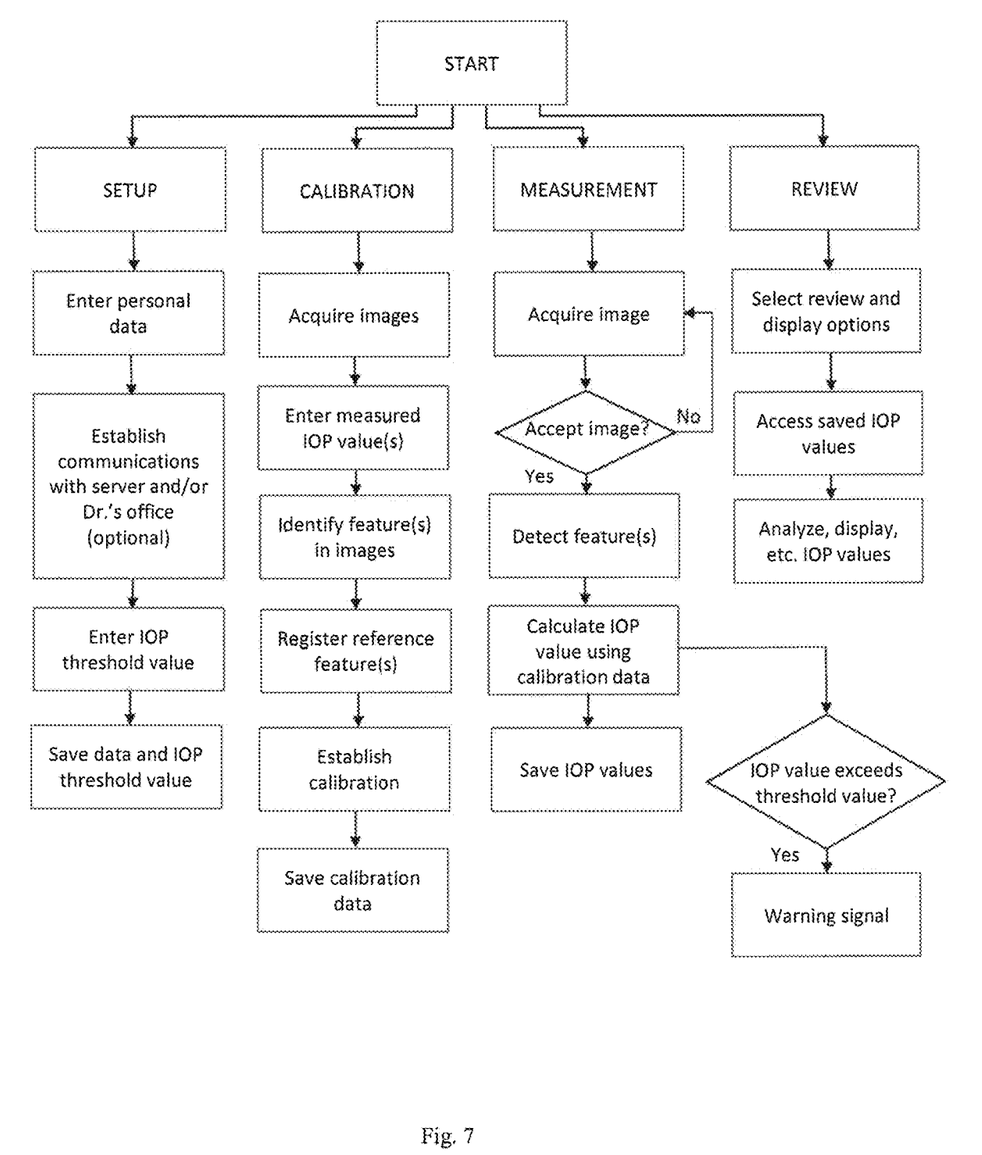
FIG. 7 is a flowchart of an algorithm for image acquisition and processing according to one embodiment.

Executing instructions may include the processor prompting the user for input at various steps, some of which are shown in FIG. 7. In one embodiment the programmed instructions may be embodied in one or more hardware modules or software modules resident in the memory of a data processing system or elsewhere. In one embodiment the programmed instructions may be embodied on a non-transitory computer readable storage medium or product (e.g., a compact disk (CD), etc.) which may be used for transporting the programmed instructions to the memory of a data processing system and/or for executing the programmed instructions. In one embodiment the programmed instructions may be embedded in a computer-readable medium or product that is uploaded to a network by a vendor or supplier of the programmed instructions, and this medium may be downloaded through an interface to a data processing system from the network by an end user or buyer.

Exemplary embodiments are described in the following non-limiting Examples.

EXAMPLE 1

Figure 1A:
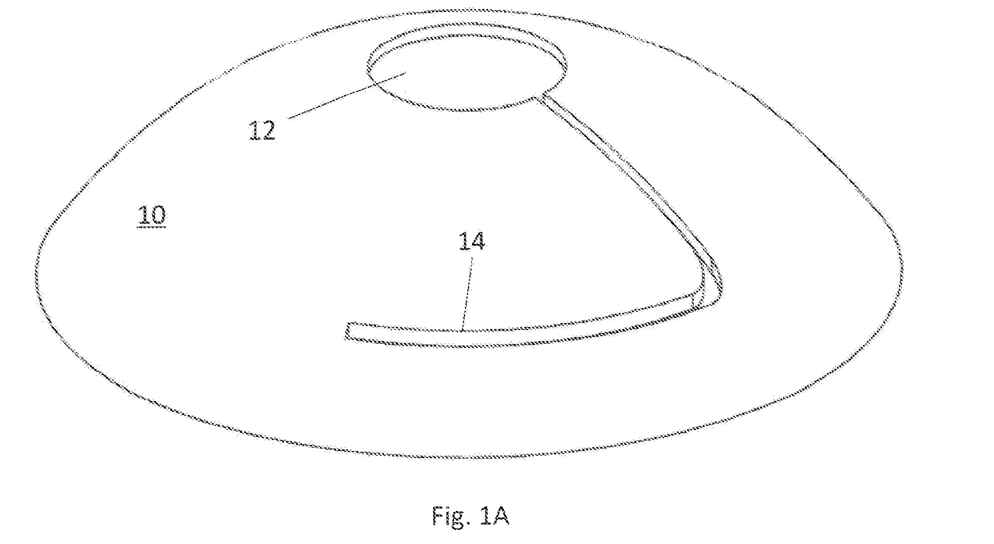
FIG. 1A shows a lens with a microchannel.
Figure 1B:
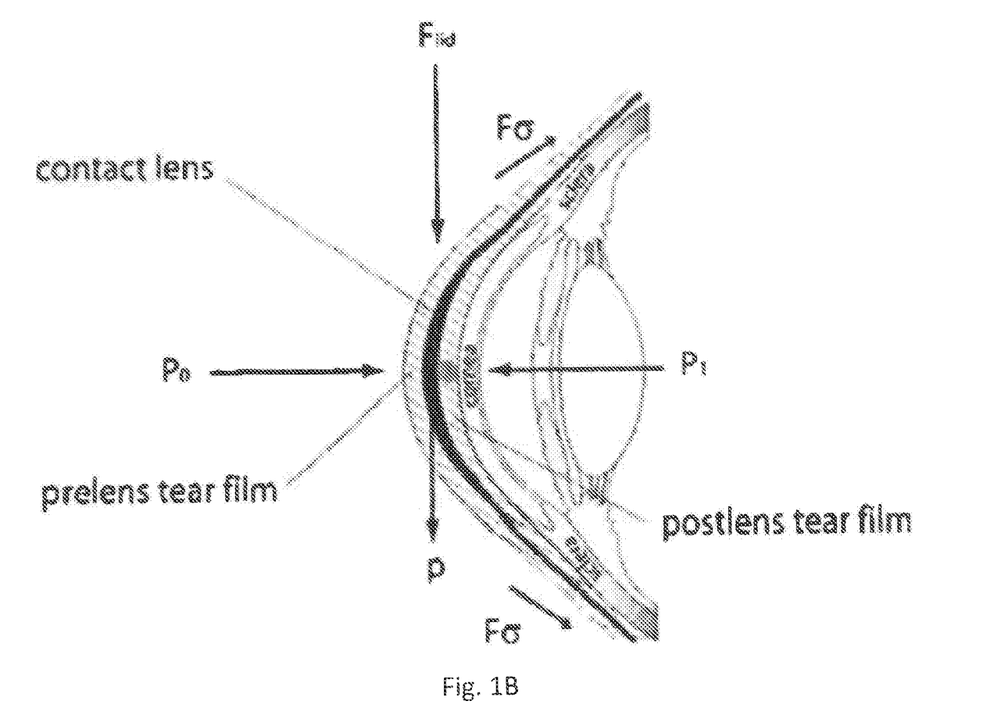
FIG. 1B is a cross-sectional view showing the device installed on an eye.
Figure 1C:
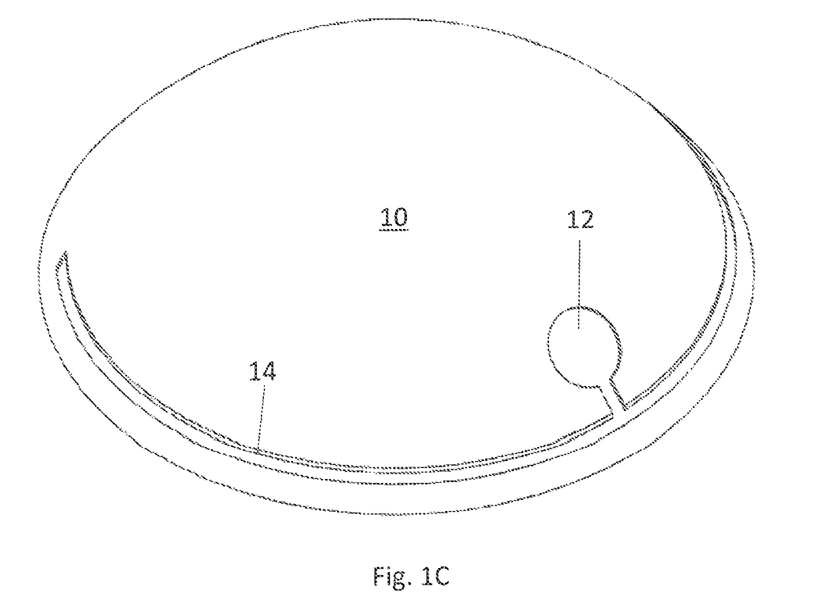
FIGS. 1C-1H are diagrams of IOP measuring devices according to various embodiments.
Figure 1D:
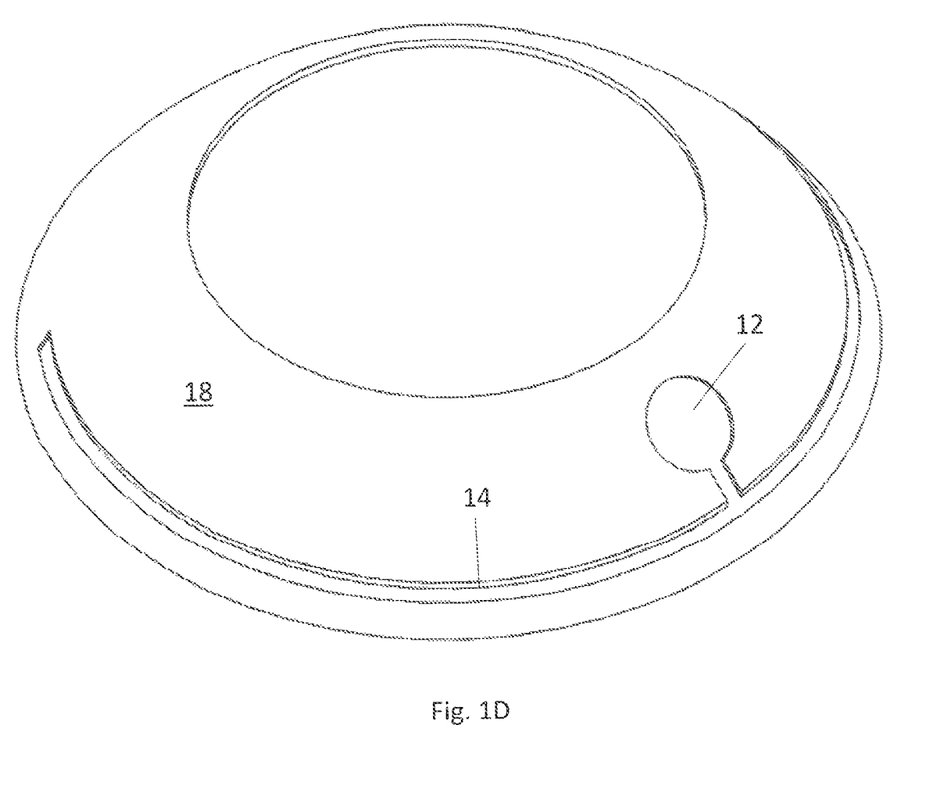
Figure 1E:
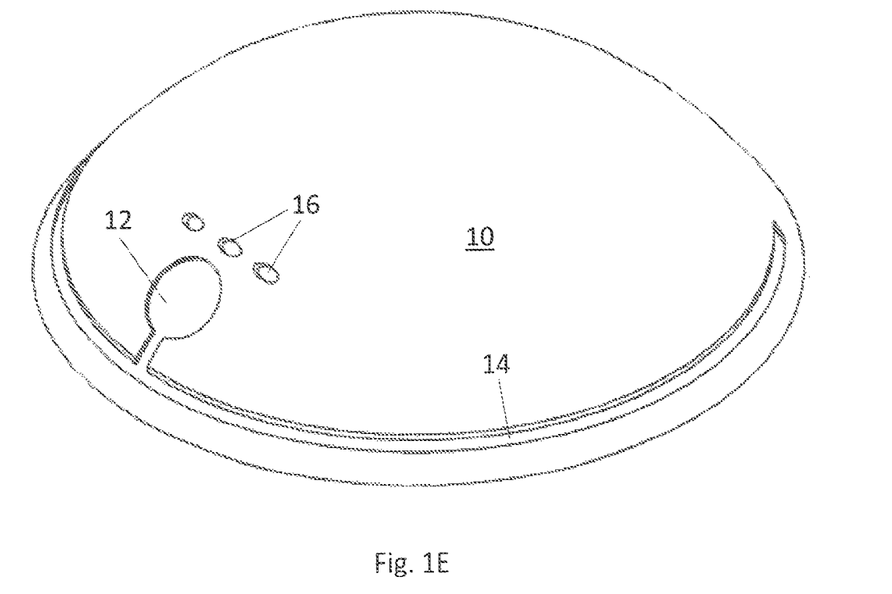
Figure 1F:
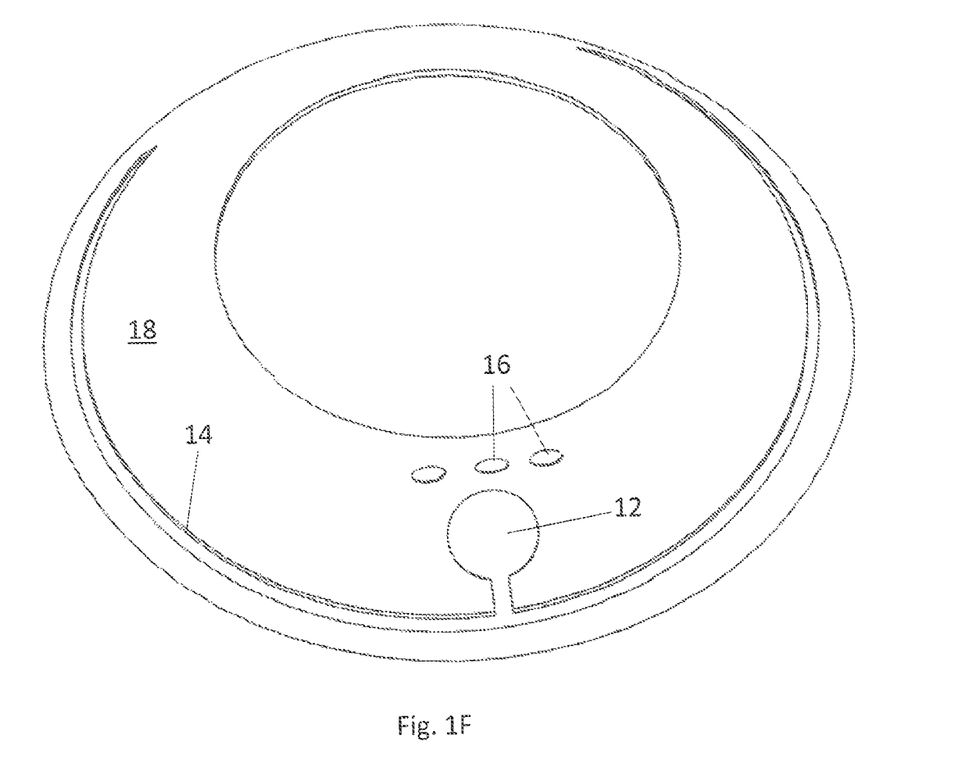

An embodiment is shown diagrammatically in FIGS. 1A and 1B. As shown in FIG. 1A, the lens has a base 10, which fits on the eye in the same manner as a typical contact lens or cosmetic lens. The microstructure includes a chamber 12 with a microchannel 14 formed therein. The base 10 may be made from an off-the-shelf contact lens or cosmetic lens, or it may be custom made. The configuration of the chamber 12 and/or microchannel 14 shown is one example of a suitable design, and it will be appreciated that other configurations geometries, shapes, locations etc.) may also be used.

Figure 1G:
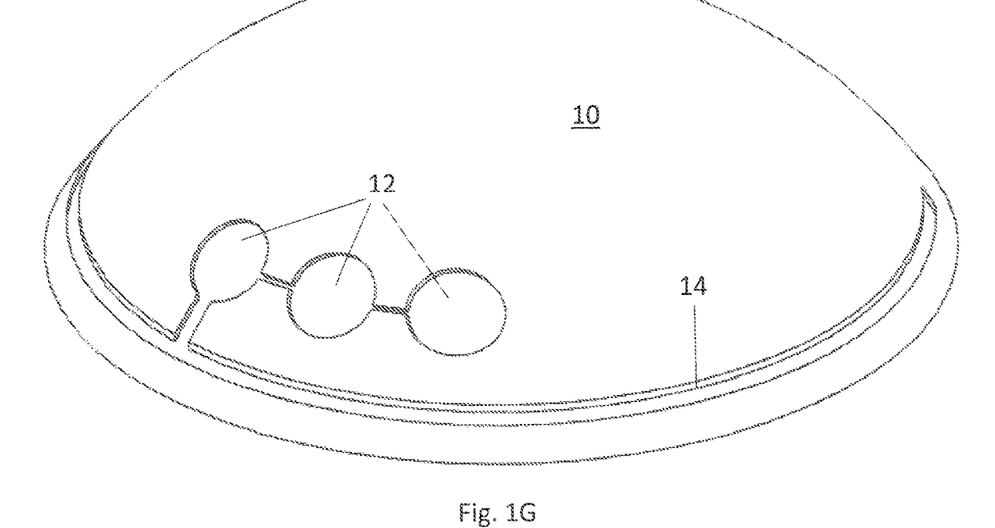
Figure 1H:
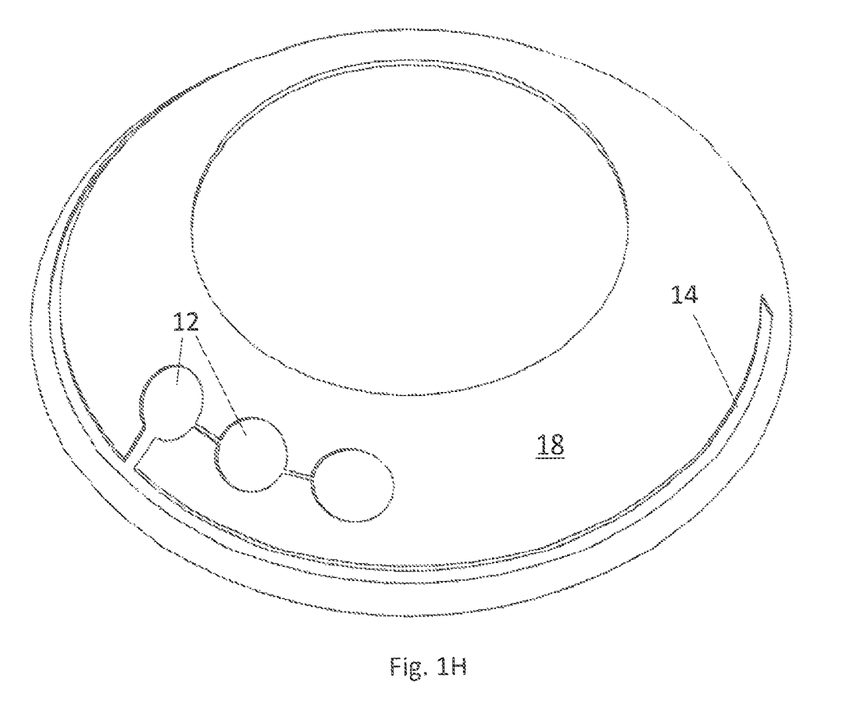

Other embodiments are shown in FIGS. 1C-1H, some of which may optionally include one or more mesh hole 16. In particular, the embodiments of FIGS. 1D, 1F, and 1H feature a lens 18 with an open central area. The open central area may substantially correspond to the cornea. Such an embodiment is expected to reduce any negative impact related to protein deposition, corneal oxygenation, or subject's vision quality. Multiple interconnected chambers 12 may be implemented as shown in the embodiments of FIGS. 1G and 1H.

In one embodiment, a cover membrane (not shown) covers the base and seals the chamber and microchannel with an indicator solution (IS). Other approaches and techniques may be used to implement the sealed chamber(s) and connected microchannel(s). The IS may be transparent (e.g., water) or a semi-transparent solution dyed to a suitable colour (e.g., light blue). The volume of the IS is calibrated to be about the same as the volume of the chamber when sealed. The IS is hydrophobic to the microchannel, which depresses the capillary effect. When the device is put on the eye, it fits to the cornea of the eye tightly under significant surface tension force Fa induced by the postlens tear film between cornea and the lens (see FIG. 1B).

In one embodiment the cover membrane may be made using a spin coater. After the base 10 and membrane are cured and bonded, a drop of silicone or PDMS may be placed onto the membrane at the center of the chamber. This drop forms a semi-sphere and is cured as a micro bump which contacts the lens and transfers force to squeeze the cover membrane on the chamber.

It is known that the cornea and sclera exhibit approximately 3 μm and 10 μm change in curvature, respectively, for each 1 mmHg intraocular pressure ($P_1$) change. This IOP induced curvature change creates a force applied on the chamber 12 which threes the IS in the chamber to disperse into the microchannel. Since the microchannel has a very small cross-sectional area, a small amount of IS thread out of the chamber due to the change of IOP fills the microchannel to a significant length. A digital image may be captured using a camera, as may conveniently be found on common electronic devices, particularly mobile or portable devices such as a smart phone, tablet, or laptop computer. A sequence of two or more images may be taken over time, and subjected to a comparison or analysis, which may employ an algorithm, to determine a change (i.e., a difference) in the position of the IS in the microchannel, relative to a reference position. A change in the subject's IOP can then be determined from the difference.

Figure 1I:
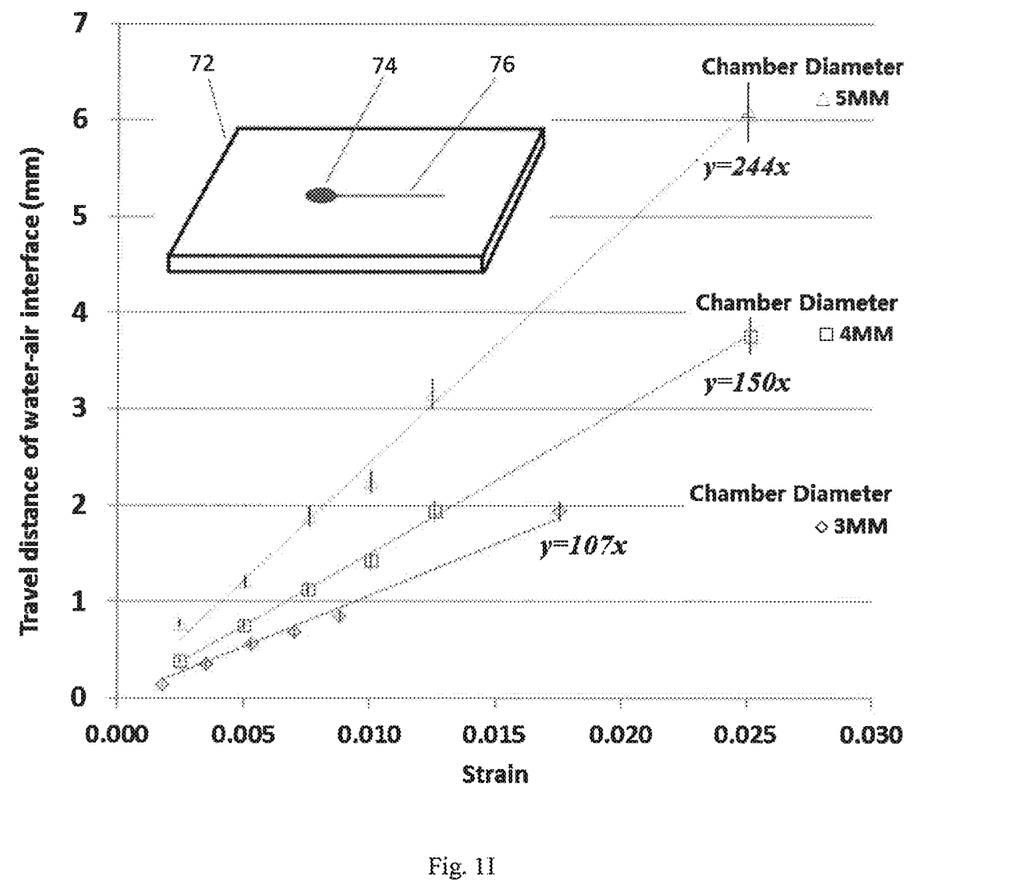
FIG. 1I is a plot showing results of tests of three sizes of a strain amplification mechanism for monitoring IOP, and a schematic of the mechanism is shown in the inset.
Figure 2A:
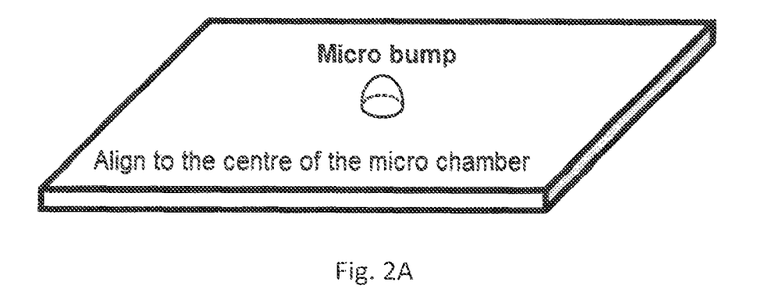
FIG. 2A shows a top seal membrane with a micro bump.
Figure 2B:
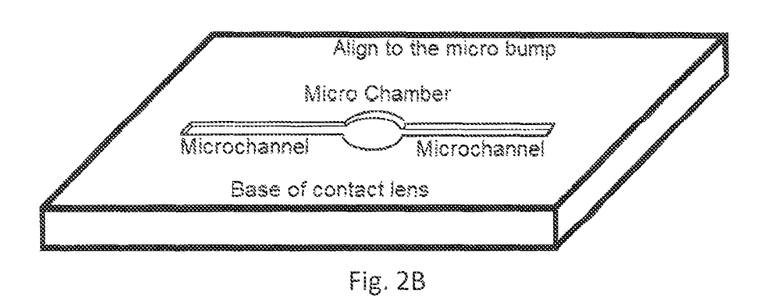
FIG. 2B shows a microchamber and microchannels on the lens.
Figure 2C:
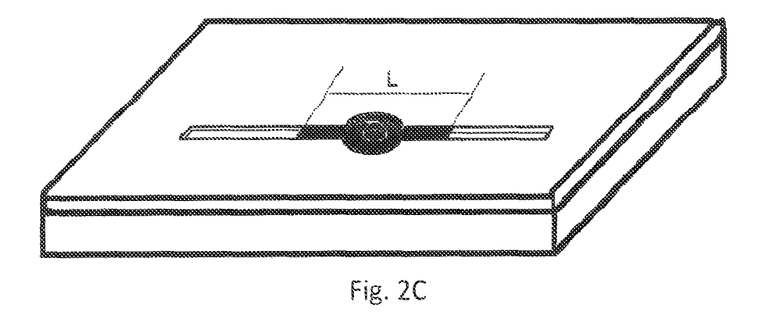
FIG. 2C shows an assembled lens with normal IOP.
Figure 2D:
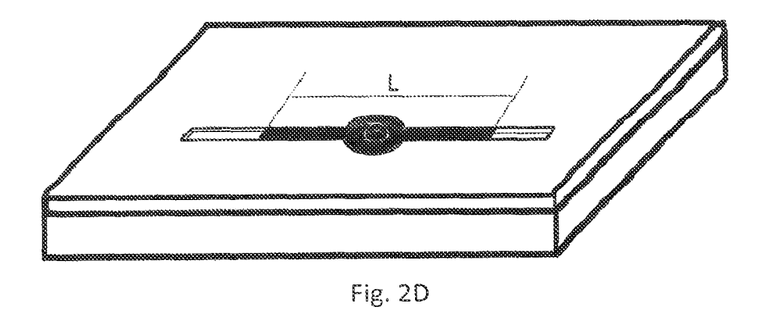
FIG. 2D shows an assembled lens under increased IOP.

Preliminary testing of embodiments was carried out with an apparatus that simulated curvature changes in response to pressure changes (i.e., induced linear deformation) and enabled a change in the microstructure to be viewed. A set of PDMS films with sealed chambers (3, 4, and 5 mm in dia., 700 μm in height) and channels (300 μm wide and 700 μm high) was prepared to investigate strain amplification. An exemplary film 72 with chamber 74 and channel 76 is shown schematically in the inset of FIG. 1I. Tensile testing was conducted for nine specimens (three for each chamber diameter). The IS travel distances were found to be over 100 times (107, 150, and 244 times, respectively) of the induced linear deformations of the chambers (see FIG. 1I). These results confirm that a lens integrated with such a strain amplifying mechanism would be able to detect an IOP change of less than 1 mmHg. Therefore, the results confirm that the embodiments are suitable for IOP monitoring.

EXAMPLE 2

Figure 3:
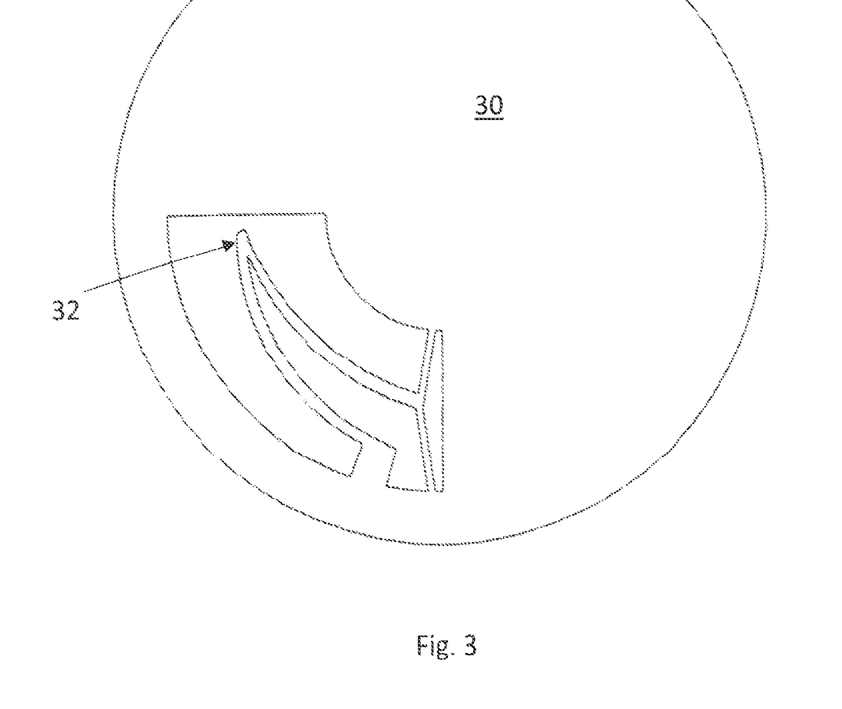
FIG. 3 is a diagram of a lens with a microstructure according to one embodiment.

Another embodiment is shown in FIG. 3. In this embodiment a contact lens or cosmetic lens 30 is modified by machining a microstructure, generally indicated at 32, into the lens. A custom made lens may also be used, and the microstructure may be incorporated into the lens during manufacturing. The microstructure, which includes a free-moving arm 34 having an end or pointer 36, behaves like a motion amplifying mechanism. The position of the arm 34 at any instant in time is related to the curvature of the lens, which is determined by the corneal curvature at that instant in time. The arm 34 moves according to a change in curvature of the lens, which is induced by a change in IOP. The movement of the arm 34 causes the tip 36 to change its position on the lens; thus, displacement of the arm is significantly amplified at the tip 36. Therefore, as in the embodiment described above, with the lens deployed on a subject's eye, digital images of lens may be captured using a camera of a smart phone or other device. A sequence of two or more images may be taken over time, and subjected to an algorithm to determine a change (i.e., a difference) in the position of the pointer 36, relative to a reference position. A change in the patient's IOP can then be determined from the difference.

The embodiment of FIG. 3 is of course one example of many possible ways to implement a microstructure based on a motion amplifying mechanism. It will be appreciated that other configurations of the mechanism and the pointer (i.e., other geometries, shapes, locations, etc.) may also be used.

Figure 4A:
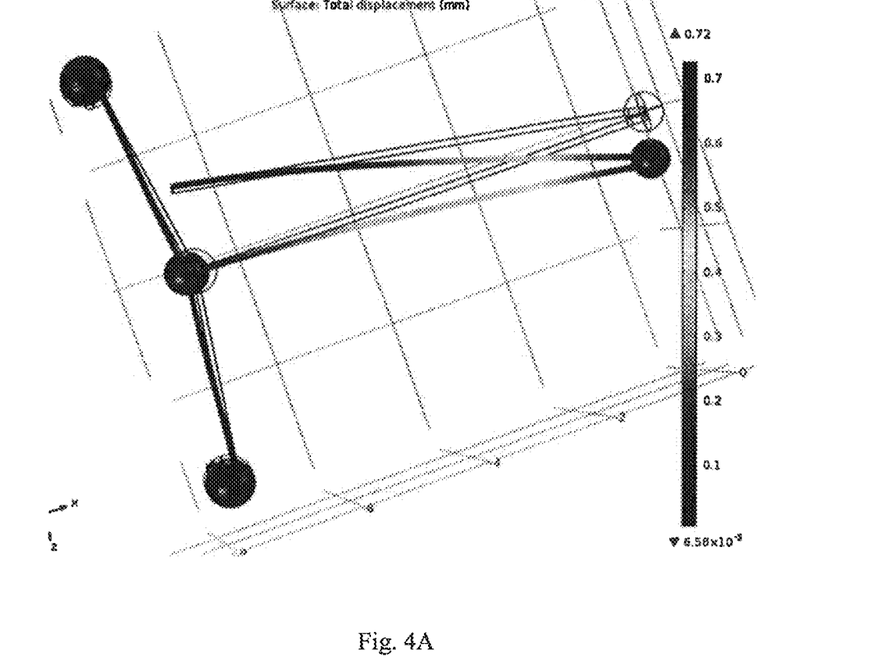
FIG. 4A is a diagram of a planar prototype used in a simulation, based on the embodiment such shown in FIG. 3.
Figure 4B:
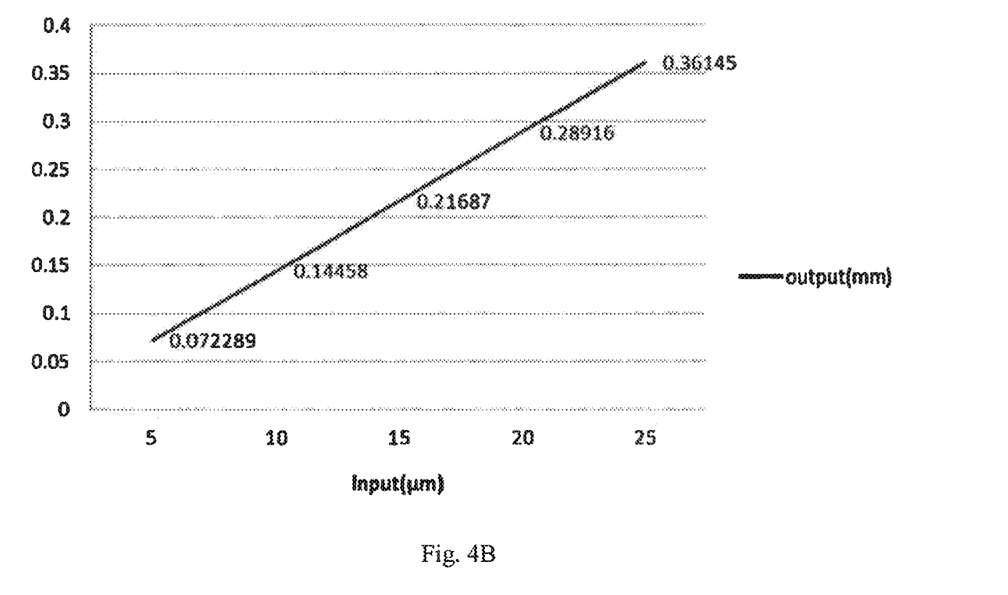
FIG. 4B is a plot showing results of the simulation.

A planar prototype was fabricated to demonstrate functionality of this embodiment. A 3D simulation was also conducted (FIG. 4A). In the simulation, with 25 μm input, movement of the tip was 360 μm, giving about 14.4 times amplification. Results of the simulation are shown in FIG. 4B. The results confirm that the embodiment is suitable for IOP monitoring.

EXAMPLE 3

Figure 5:
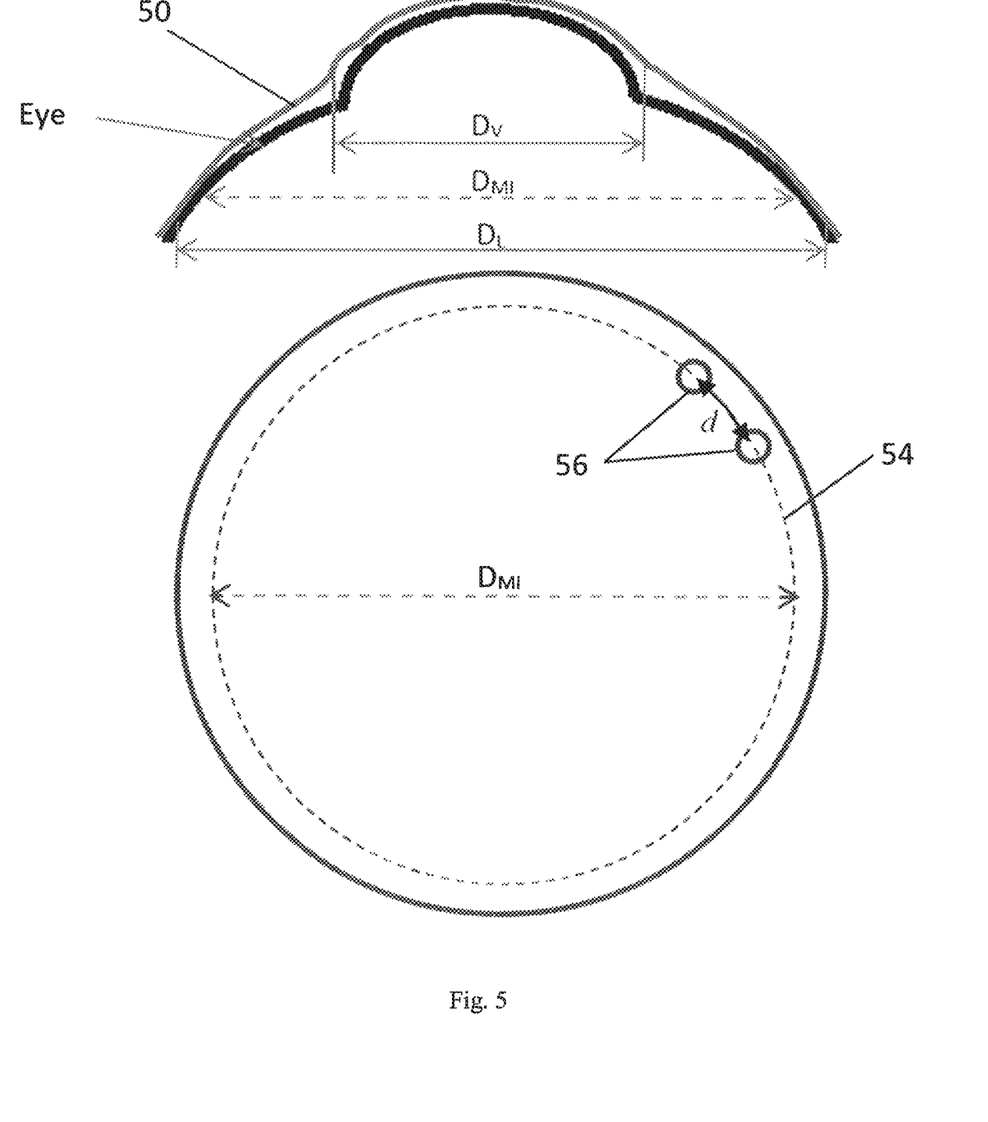
FIG. 5 is a diagram of a lens in cross-section (upper) and plan (lower) views, with a microstructure according to one embodiment.

Another embodiment is shown in FIG. 5. In this embodiment a contact lens or cosmetic lens was modified by disposing a microstructure in or on the lens. A custom made lens may also be used, and the microstructure may be incorporated into the lens during manufacturing. In this example various dimensions are recited for illustrative purposes. It will be appreciated that other dimensions may be used.

Referring to FIG. 5, a lens 50 has an overall diameter $D_L$ of ~15 mm. The lens has a vault (i.e., an outwardly extending portion) that substantially corresponds to the cornea of the eye. The vault portion has a diameter $D_v$ that may be approximately one-half of the overall diameter of the lens $D_L$, which provides ~3.5 mm wide area of the lens surrounding the vault. The microstructure comprises a pair of markers 56 in the 3.5 mm wide area of the lens. In this embodiment the markers are holes; however, it will be appreciated that other markers could be used. The holes are located along a motion indicator circle 54 having a diameter $D_{MI}$ of ~13.5 mm. The center-to-center distance d between the adjacent holes on the motion indicator circle is ~1.3 mm. The diameters $D_V$, $D_{MI}$, and $D_L$ may be substantially concentric.

The eye diameter is approximately 26 mm. The curvature change rate of the sclera is about 100 μm/mmHg, which gives a strain of $\varepsilon=100/13000$ on the sclera. A distance d of 1.3 mm between the two holes yields a deformation $\Delta d = d \times \varepsilon = 1300 \times 100/13000 = 10$ μm, i.e., the distance between the two holes will change at a rate of 10 μm/mmHg. If the distance d between the two holes is doubled to 2.6 mm, then the corresponding deformation rate will be 20 μm/mmHg. The distance d between two holes can be increased or decreased as desired for a given design, or to improve detection based on the resolution of a selected camera, A further embodiment, shown in FIG. 6A, was implemented in a soft contact lens 60 by creating a pattern in the lens with four markers (in this case, holes) 62a-62d arranged in an outer ring 62 and four markers 64a-64d arranged in an inner ring 64. The outer and inner rings 62, 64 are analogous to the motion indicator circle 54 in the embodiment of FIG. 5. Preliminary tests were conducted by mounting the embodiment on a balloon, and analyzing changes in the distances between holes as the inflation of the balloon was varied. The distances were analyzed using imaging software. As expected, the increase in distance between holes, as balloon pressure increased, was greater for the holes in the outer ring than for holes in the inner ring. The results confirm the suitability of these embodiments for measuring and monitoring IOP.

As noted above, features other than holes in the lens may also be employed. For example, markers created with dye or pigment may be disposed on the lens and would function similarly to holes as detectable features.

Figure 6A:
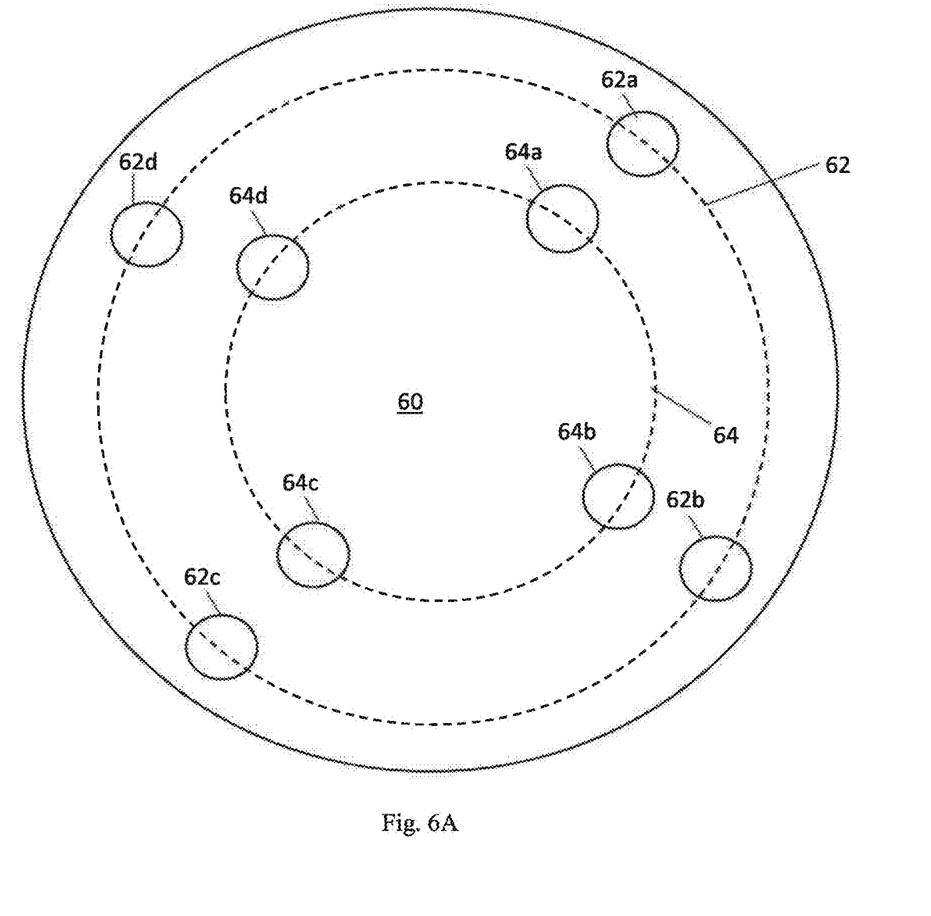
FIGS. 6A and 6B are diagrams of lenses with microstructures according to various embodiments.
Figure 6B:
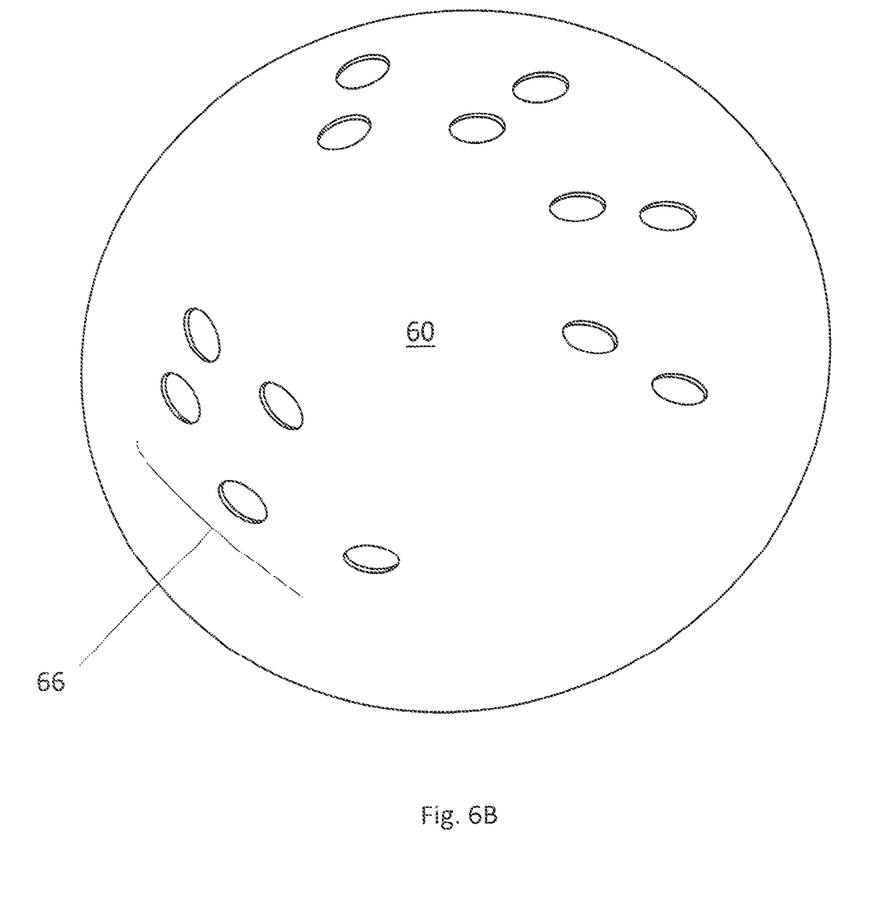

The embodiment of FIG. 6B is similar to that shown in FIG. 6A, except that a reference structure 66 or image is included to provide scale. The reference structure 66 or image is of substantially constant size and/or shape and/or position regardless of the change in curvature of the lens 60, so that a change in the lens curvature in response to a change in IOP can be quantified. The reference structure may be made from a material with a Young's modulus that is much higher than that of the lens (e.g., PDMS, or silicone hydrogel). For example, a fine gold wire or suture (e.g., diameter=0.03 mm) of selected length may be embedded in the lens as shown in FIG. 6B. The length of the wire or material will not vary significantly When the lens changes curvature due to a change in IOP, and therefore it can be used as a constant length reference to provide the scale (e.g., pixels, microns, etc.) during image processing. This avoids the need for a reference image and simplifies acquiring and processing images.

EXAMPLE 4

An application running on a mobile computing device such as a smartphone may be used to analyze images of an IOP measuring device as described herein, and provide an output comprising an indication of the subject's IOP at a given time, and/or of a change in in IOP over time. The application includes software implemented on the mobile device. In one embodiment, the software has two components: (1) an imaging processing algorithm; and (2) a data management algorithm. The data management algorithm may communicate with a remote server located in a physicians' office or a hospital, to perform functions such as uploading data to the remote server. In one embodiment the software may be implemented in Java, and Objective-C may be used to for Android and iOS-based mobile devices. In one embodiment C# and asp.net may be used to develop data management programs on the server, and the database may be created and maintained using MS SQL.

At least a part of the application may be implemented according to an algorithm such as the embodiment shown in FIG. 7.

(1) Image Processing Algorithm. This algorithm may include several functions, such as setup, image taking, pattern searching, data managing, and graphical presentation. When the application is launched, it may provide four tabs: Setup, Calibration, Measurement and Review. The Setup tab allows the user (i.e., subject, patient) to setup their personal profile, such as, name, gender, age, personal IOP threshold value, remote server serial number, etc., which together with variables such as measured IOP, time stamp, activity at the time of measurement, are sent to the remote data server. An encrypted format may be used to protect patient privacy. The Calibration tab allows the user to take two or more images of the location of an indicator (e,g., water/air interface) in each IOP monitoring lens before wearing it and after wearing it for the first time. The user is then asked to enter the corresponding IOP recently measured by a clinician (professional optometrist or vision care physician), and to define a pattern for searching, e.g., by drawing small square enclosing the indicator feature(s). Markers for scale reference (e.g., different shapes such as triangles and rectangles) may be registered automatically. For each image, the program determines dimension scales from the pixels between two adjacent markers. A correlation between the indicator feature travel distance and IOP for the lens is calibrated based on these images. From these images, the program identifies the location of an indicator feature from a reference point at zero and the current IOP. The ratio of indicator travel distance vs. IOP is identified and used to adjust a ratio table generated from pre-calibration data for better accuracy. The pre-calibration data establishes the form of the relationship between indicator feature travel distance and IOP for use in combination with an observed calibration point. Optionally, additional data points may be added from further visits to an eye care clinician when the patient has a different IOP to further refine the measurement accuracy.

In the Measurement tab, a user is asked to take images with the IOP lens centered and focused in the target frame on the screen. When a proper image is taken, the algorithm searches for the position of the indicator feature and calculates the corresponding IOP value using the known adjustment ratio. The user is then able to select activity from a drop list, or enter his/her activity. The IOP value, measured time, and activity at the time is recorded in the mobile device locally, and together with the user's personal information is sent to the remote server after being confirmed by the patient through encrypted text message. If the measured IOP is higher than the threshold value in the setup, a warning signal will appear to warn the patient, In the Review tab, the user can browse all his/her measured IOP values in a tabular or graphic format with, e.g., 30 values plotted in the active window with their time stamps. However, the user can scroll back and forth to review the all the data, which gives the user direct observation of the IOP trend. This can even be helpful for users to form an interest in their vision health and enhance adherence to therapy.

(2) Data Management Algorithm. In this algorithm a user can setup multiple threshold values according to his/her physician's advice. If a warning message is triggered, it will be sent to the server for recording. On the server side, the database may have several main tables, including a patient-information table, measured IOP table, physician-information table, medication table, etc. Each user is given a unique ID, used as a primary key in the patient-information table and measured IOP table. It is a foreign key for other tables. On the server, a data receiving program and a GPRS message modem are used to receive messages from all patients. Received messages are passed to the data receiving program on the server. The program decodes and analyzes the sender's information and stores the data in the database accordingly, If a warning message is found, the server sends the information to the physician immediately so that the physician can take timely and proper medical action to help the user. On the server, a web-server program (e.g., using C#, B/S frame work) provides clinicians such as physicians or other authorized medical care professionals a login interface requiring user ID and password. When they login to the program, they are able to see their patients' data. They can select a patient from the list and review their IOP values in graphic format or table chart, as well as their medical history, including appointments, treatment etc. The web program may be published on the server, so that physicians and medical professionals can remotely access it through an internet browser via a secure route.

All cited documents are incorporated herein by reference in their entirety.

EQUIVALENTS

Those of ordinary skill in the art will recognize, or be able to ascertain through routine experimentation, equivalents to the embodiments described herein. Such equivalents are within the scope of the invention and are covered by the appended claims.

The invention claimed is:

1. A device for monitoring intraocular pressure (IOP) of a subject, comprising:
   a non-invasive lens that is adapted to fit on the subject's eye;
   a strain-amplifying microstructure disposed in or on the lens, including a sealed chamber and connected microchannel, and an indicator solution that fills a length of the connected microchannel;
   wherein the strain-amplifying microstructure exhibits a change in shape and/or geometry and/or position on the lens in response to a change in curvature of the lens;
   wherein the lens is adapted to change curvature in response to a change in IOP;
   wherein the length of the microchannel filled with the indicator solution changes according to the change in curvature to the lens;
   wherein the change in length of the microchannel that is filled with the indicator solution is detectable in digital images of the lens, or of a part of the lens, and indicates a change in IOP.

2. The device of claim 1, further comprising a reference structure:
   wherein the reference structure has a selected size and/or position and/or shape that is substantially constant irrespective of a change in curvature of the lens in response to a change in IOP.

3. The device of claim 1, wherein the digital images are captured using a digital camera of a personal electronic device.

4. The device of claim 3, wherein the personal electronic device is a smartphone.

5. A method for monitoring intraocular pressure (IOP) of a subject, comprising:

disposing a strain-amplifying microstructure in or on a lens that is adapted to fit on the subject's eye, the strain-amplifying microstructure including a sealed chamber and connected microchannel, and an indicator solution that fills a length of the connected microchannel, wherein the strain-amplifying microstructure exhibits a change in shape and/or geometry and/or position on the lens in response to a change in curvature of the lens, wherein the curvature of the lens changes in response to a change in IOP;

obtaining two or more digital images of the lens, or a part of the lens, at two or more instants in time;

detecting a change in the length of the microchannel filled with the indicator solution in the digital images; and correlating the change in the length of the microchannel filled with the indicator solution with a change in IOP.

6. The method of claim 5, further comprising quantifying a change in the length of the microchannel filled with the indicator solution in the digital images using a reference structure:

wherein the reference structure is embedded or integrated in the lens and has a selected size and/or position and/or shape that is substantially constant irrespective of a change in curvature of the lens in response to a change in IOP.

7. The method of claim 5, wherein the digital images are captured using a digital camera of a personal electronic device.

8. The method of claim 7, wherein the personal electronic device is a smartphone.

* * * * *